United States Patent
Ashish et al.

(10) Patent No.: US 11,313,815 B2
(45) Date of Patent: Apr. 26, 2022

(54) IN VITRO METHOD FOR DETECTING ACTIVE MYCOBACTERIUM TUBERCULOSIS USING HAIR SMALL ANGLE X-RAY SCATTERING PROFILE

(71) Applicant: Council of Scientific & Industrial Research, New Delhi (IN)

(72) Inventors: Ashish, Chandigarh (IN); Ashwani Kumar, Chandigarh (IN); Amin Sagar, Chandigarh (IN)

(73) Assignee: COUNCIL OF SCIENTIFIC & INDUSTRIAL RESEARCH, New Delhi (IN)

(*) Notice: Subject to any disclaimer, the term of this patent is extended or adjusted under 35 U.S.C. 154(b) by 0 days.

(21) Appl. No.: 16/463,487

(22) PCT Filed: Nov. 21, 2017

(86) PCT No.: PCT/IN2017/050547
§ 371 (c)(1),
(2) Date: May 23, 2019

(87) PCT Pub. No.: WO2018/096557
PCT Pub. Date: May 31, 2018

(65) Prior Publication Data
US 2019/0360950 A1  Nov. 28, 2019

(30) Foreign Application Priority Data
Nov. 23, 2016  (IN) .............................. 201611039949

(51) Int. Cl.
*G01N 23/201* (2018.01)
*G01N 33/483* (2006.01)

(52) U.S. Cl.
CPC ....... *G01N 23/201* (2013.01); *G01N 33/4833* (2013.01); *G01N 2223/612* (2013.01)

(58) Field of Classification Search
CPC ...... G01N 23/00; G01N 23/04; G01N 23/201; G01N 33/483; G01N 33/4833; G01N 2223/612; A61B 6/48; A61B 6/483
See application file for complete search history.

(56) References Cited

FOREIGN PATENT DOCUMENTS

| WO | WO-2010/126856 A1 | 11/2010 |
| WO | WO-2011/138765 A1 | 11/2011 |

OTHER PUBLICATIONS

International Search Report for PCT/IN2017/050547 dated Mar. 9, 2018 (4 pages).
P. Saegnkaew et al. "A Preliminary X-Ray Study on Human-Hair Microstructures for a Health-State Indicator" Internal Journal of Biomedical and Bilogical Engineering, Nov. 1, 2011, pp. 630-634.
(Continued)

*Primary Examiner* — Jurie Yun
(74) *Attorney, Agent, or Firm* — Blank Rome LLP

(57) ABSTRACT

The present invention relates to an in-vitro method of detecting Mtb infection by using SAXS profile of hair sample. The invention is an approach to overcome the problem of non-invasively and cost-effectively yet reliably diagnosing presence of active tuberculosis in the patient. There would be no risk to the sample handlers getting infected from the sample, cross-contamination of samples, low cost and quick turn-around time of diagnosis.

5 Claims, 5 Drawing Sheets

(56) References Cited

OTHER PUBLICATIONS

Michael Eisenhut et al. "Hair Analysis for Determination of Isoniazid Concentrations and Acetylator Phenotype during Antituberculous Treatment", Tuberculosis Research and Treatment vol. 2012, Jan. 1, 2012, pp. 1-6.

Jean Doucet et al. "Micron-scale assessment of molecular lipid organization in human stratum corneum using microprobe X-ray diffraction", Journal of Lipid Research, vol. 55. No. 11, Sep. 1, 2014, pp. 2380-2388.

Pal, R., Hameed, S., Kumar, P., Singh, S., and Fatima, Z. (2017) Comparative lipidomics of drug sensitive and resistant Mycobacterium tuberculosis reveals altered lipid imprints. 3 Biotech 7, 325.

IN VITRO METHOD FOR DETECTING ACTIVE MYCOBACTERIUM TUBERCULOSIS USING HAIR SMALL ANGLE X-RAY SCATTERING PROFILE

RELATED APPLICATIONS

This application is a national phase application of PCT/IN2017/050547, filed Nov. 21, 2017, which claims priority to Indian Application No. IN 201611039949, filed Nov. 23, 2016. The entire contents of those applications are incorporated herein by reference.

FIELD OF THE INVENTION

The present invention relates to an in-vitro method for detecting active *Mycobacterium tuberculosis* (Mtb) infection in host by using small angle X-ray scattering (SAXS) profile of the hair sample. The method will have implications in using SAXS profiles for identifying patient status relative to Mtb infection and tracking efficacy of the anti-*tuberculosis* therapy regime being given to a patient.

BACKGROUND OF THE INVENTION

The present invention addresses an unmet medical need of identifying presence of active *tuberculosis* in our bodies in a cost, time and certainty manner with least probability of cross-contamination of sample, little sample manipulation or processing, and with minimal discomfort to the sample provider. Though *tuberculosis* infection claims largest number of human lives each year, there is little improvement in the early and/or rapid diagnosis of this disease. Primary diagnosis protocols persistent today include staining of sputum smears, skin tests for response against pure protein derivative (PPD), X-rays transmission images of chest, imaging of other parts of body, and analysis of blood, spinal fluid or samples of other tissues etc. for PCR based amplification of markers of Mtb. It has been established that Mtb infection alters global lipid profile in host and it has been detected using lipidomics studies (Jain M. et al. 2007), and more recently (Pal R, et al. 2017), amongst others. It is pertinent to mention here that none have characterized lipid content in hair and its organization prior to our research work.

Most techniques have evolved some advantages but suffer from many limitations like:

1. Inability to provide a quantitative measure.
2. Cannot be termed as an early stage diagnostic.
3. Use samples which can infect others.
4. Use samples and methodologies prone to cross-contamination.
5. Use samples and methodologies which require meticulous and extended sample processing.
6. Use methodologies where samples perish and cannot be re-analyzed.
7. Very few methods give a read-out of response to short-term medication.
8. Costs of reliable protocols are non-affordable to most, and rely on government subsidies.
9. Time duration of performing the test(s) from the point of sample collection need sincere reduction.

Bearing in mind that: 1) *tuberculosis* alters global lipid profile, and 2) lipid profile in hair and changes in that aspect can be analyzed non-invasively and with certainty by analyzing hair SAXS profiles, we explored SAXS pattern of hair from patients who were orthogonally confirmed to be Mtb +ve and −ve. Our results presented in the examples support that: 1) yes, there are signature changes in the SAXS pattern of scalp hair in Mtb −ve and +ve patients, and 2) to the best of our knowledge and experiments, these signatures are specific to Mtb infection and cannot arise from exposure of hair to regular cosmetic treatments.

BRIEF DESCRIPTION OF THE DRAWINGS

FIG. 1: Representative SAXS profile of 120 informed donors not suffering from any ailment highlighting the presence of mainly two peaks in the range being studied. Also, real dimensions and structural features in hair from which these peaks arise have been described.

FIG. 2: SAXS profiles of five different scalp hairs of four different donors are presented which clearly showed that there is no significant difference in different hairs of same individual.

FIG. 3: SAXS profiles of hair from three donors before and after treatment with commercial shampoo, bleach, color, heat and cold formic acid treatment showed that first three commonly used cosmetic treatments do not alter the peak profiles.

FIG. 4: This figure shows the position of the peak expected near 1.38 $nm^{-1}$ in reciprocal space or 4.55 nm in real space in the SAXS profiles of the hairs from Mtb −ve and +ve patients as confirmed by orthogonal methods like PPD, sputum smear and PCR based methods. Some samples were also studied from close contacts of Mtb +ve patients. Four samples shown as blue dots represent repetition of hair samples from Mtb +ve patients after a month of collection, and the close by green triangle represents the shifted position of their peak profile after a month of Mtb therapy.

FIG. 5: This figure shows the data processing flow being followed to interpret if SAXS profile of scalp hair could be a read-out for presence or absence of active *tuberculosis* in host.

OBJECT OF THE INVENTION

The main object of the present invention is to provide an in-vitro method for detecting *tuberculosis* infection by using SAXS profile of hair.

Another object of the present invention is to provide possible tracking of effectiveness of anti-*tuberculosis* therapy in a time-dependent manner.

SUMMARY OF THE INVENTION

Accordingly, the present invention relates to an in-vitro method of detecting Mtb infection by using SAXS profile of hair sample. The invention is an approach to overcome the problem of non-invasively and cost-effectively yet reliably diagnosing presence of active *tuberculosis* in the patient.

In an embodiment of the present invention, there is provided a non-invasive in-vitro method for detecting active *Mycobacterium tuberculosis* (Mtb) using small angle X-ray scattering (SAXS) of a hair sample, said method comprising the steps of:

- a. mounting the hair sample in the SAXS sample holder;
- b. aligning the hair sample with X-ray beam on an integrated mobile platform using a read-out at three PIN diodes wherein the integrated mobile platform allows alignment and data collection in antomated manner from ten hair samples;
- c. acquiring SAXS data from the hair sample;

d. analyzing peak profiles arising from keratin and lipid content in the hair sample; and
e. analyzing positions of two peaks in the hair sample wherein presence of keratin peak maxima at 0.78 nm$^{-1}$ or 8.05 nm, and presence of lipid peak above or below the range of 1.28-1.48 nm or 8.85-7.57 nm confirms the presence of active Mtb.

In an embodiment of the present invention, there is provided a non-invasive in-vitro method for detecting active *Mycobacterium tuberculosis* (Mtb) wherein SAXS is performed using a source of monodisperse X-rays with optics selected from a group having line, point, elliptical and rectangle collimation of X-rays on sample and data.

In an embodiment of the present invention, there is provided a non-invasive in-vitro method for detecting active *Mycobacterium tuberculosis* (Mtb) wherein data is collected on a detector of X-rays selected from the group consisting of X-ray sensitive films, CCD, 1D, and 2D detector.

In an embodiment of the present invention, there is provided a non-invasive in-vitro method for detecting active *Mycobacterium tuberculosis* (Mtb) wherein for point or elliptical source collimation, the hair sample is mounted in a sample holder using a single pin diode before detector as a guide.

In an embodiment of the present invention, there is provided a non-invasive in-vitro method for detecting active *Mycobacterium tuberculosis* (Mtb) wherein the hair sample is in the range of 3 cm to 4 cm in length.

In an embodiment of the present invention there is provided a non-invasive in-vitro method for detecting active *Mycobacterium tuberculosis* (Mtb) wherein for line source collimation, a sealed tube source is used.

In an embodiment of the present invention, there is provided a non-invasive in-vitro method for detecting active *Mycobacterium tuberculosis* (Mtb) wherein parameters of the method are such as to avoid skewing of scattering profile to avoid improper alignment of the hair sample in terms of sample to detector distance and incident.

In an embodiment of the present invention, there is provided a non-invasive in-vitro method for detecting active *Mycobacterium tuberculosis* (Mtb) wherein there is no cross-contamination in the hair sample and the sample can be transported to the site of examination.

In an embodiment of the present invention, there is provided a use of the method to monitor the progress or response of patients to different anti-Mtb therapies as a function of time and/or medication.

DETAILED DESCRIPTION OF THE INVENTION

The present invention relates to the use of Small Angle X-ray Scattering (SAXS) profiles of body hair including scalp hair, to predict the presence or absence of active *tuberculosis* in the host. Inventive steps included acquiring SAXS data from hair of *Mycobacterium tuberculosis* (Mtb) positive and negative patients, and analyzing the peak profiles arising from keratin and lipid content in hair using in-house SAXS instrument and programs. The present application disclose a SAXS based screening method where host is Mtb infection negative, if one peak is arising from keratin has maximum within 0.71-0.83 $nm^{-1}$ or 8.85-7.57 nm, respectively and the other peak from lipid has maximum between 1.28-1.48 $nm^{-1}$ or 4.91-4.24 nm, respectively. Alternatively, if the keratin peak is within same limits, but the lipid peak has maxima below 1.28 $nm^{-1}$ or higher than 4.91 nm, or higher than 1.48 $nm^{-1}$ or lower than 4.24 nm, then as per the analysis, that sample provider is Mtb positive. The present application also uses ratio of the two peaks to analyze which results can be confidently concluded, and the protocol is valid for any collimation of SAXS source on sample point, line or any other, and for in-house and/or synchrotron sources.

According to the present invention, SAXS profile of body hair including scalp hair can be acquired and analyzed to screen which patient has active Mtb infection. There would be no risk to the sample handlers getting infected from the sample, cross-contamination of samples, low cost and quick turn-around time of screening. The inventive step of the process includes: 1) designing and functionalizing mounts to acquire SAXS data from hair samples using a sealed tube X-ray set-up or in-house source (but not limited to this optical design or adaption at synchrotron sources), 2) writing programs for automated alignment of hair samples with X-ray beam, 3) writing and testing software for automated data collection, processing of SAXS data and 4) software for analysis of SAXS data and prediction of presence/absence of *tuberculosis* induced changes in SAXS profile.

In accordance with the present application, the SAXS profiles of scalp hair from non-infected Mtb patients have been shown which indicates that essentially there are two main peaks arising from hair samples in SAXS region, one with maxima close to q value of 0.78 $nm^{-1}$ or 8.05 nm in real space and other maxima close to 1.38 $nm^{-1}$ in reciprocal space or 4.55 nm in real space. The present application has examples providing data to support that all scalp hairs have same scattering profile regardless of their collection site, and regular cosmetic treatments do not alter the SAXS profiles. When extended to Mtb +ve patients and their close contacts with no detectable infection, the SAXS profiles brought forth that in confirmed Mtb +ve patients, though the peak maxima near 0.78 $nm^{-1}$ or 8.05 nm does not change in its position, the second peak maxima close to 1.38 $nm^{-1}$ or 4.55 nm shifts towards higher or lower q values in reciprocal space or lower or higher in real space, respectively. Based on literature analysis, it is pertinent to emphasize here that though this application is the first to use in-house X-ray source to obtain SAXS profiles of hairs and correlate the differential behavior with active Tb infection, the methodology of the present application is extendable to other optical alignment of SAXS including point or line source, and can be executed at synchrotron source.

The process of the present application involves:

1) Sample collection: After informing the patient about the procedure and anticipated results, interested or prescribed for screening/diagnostics as per extant guidelines, hair from patient is taken by plucking. The sample is coded and kept in tagged pouch for screening.

2) On-site Screening/Courier and storing: The samples are to be stored in non-humid conditions, even at ambient room temperature till data collection either on-site or can be couriered to the site of analysis.

3) SAXS data collection: The hair samples are loaded in the stage to be aligned in the X-ray beam. Alignments are done using read-out at three PIN diodes. After alignment, data is collected for 10 minutes. The sample to detector is maintained in a manner that data is collected 0.01 to 2.1 $nm^{-1}$ in reciprocal space or 628 to 3.14 nm in real space, but not limited to this range as most of the data collection pertinent to the range required for the analysis claimed here. Any source, micro-focus or sealed tube or rotating anode or synchrotron source with collimation on sample—line, point, elliptical or rectangle can be used. The data can be acquired on any detector—X-ray responsive image plate, CCD or equivalent or superior detector. For the present application, all data is collected using line collimated X-ray aligned on hair (SAXSpace, Anton Paar) and orthogonally positioned 1D CMOS detector (Mythen from Dectris). The acquired intensity profile data is corrected for the beam position and distilled out in three column format –q, I(q) and dI(q).

Figure 5:
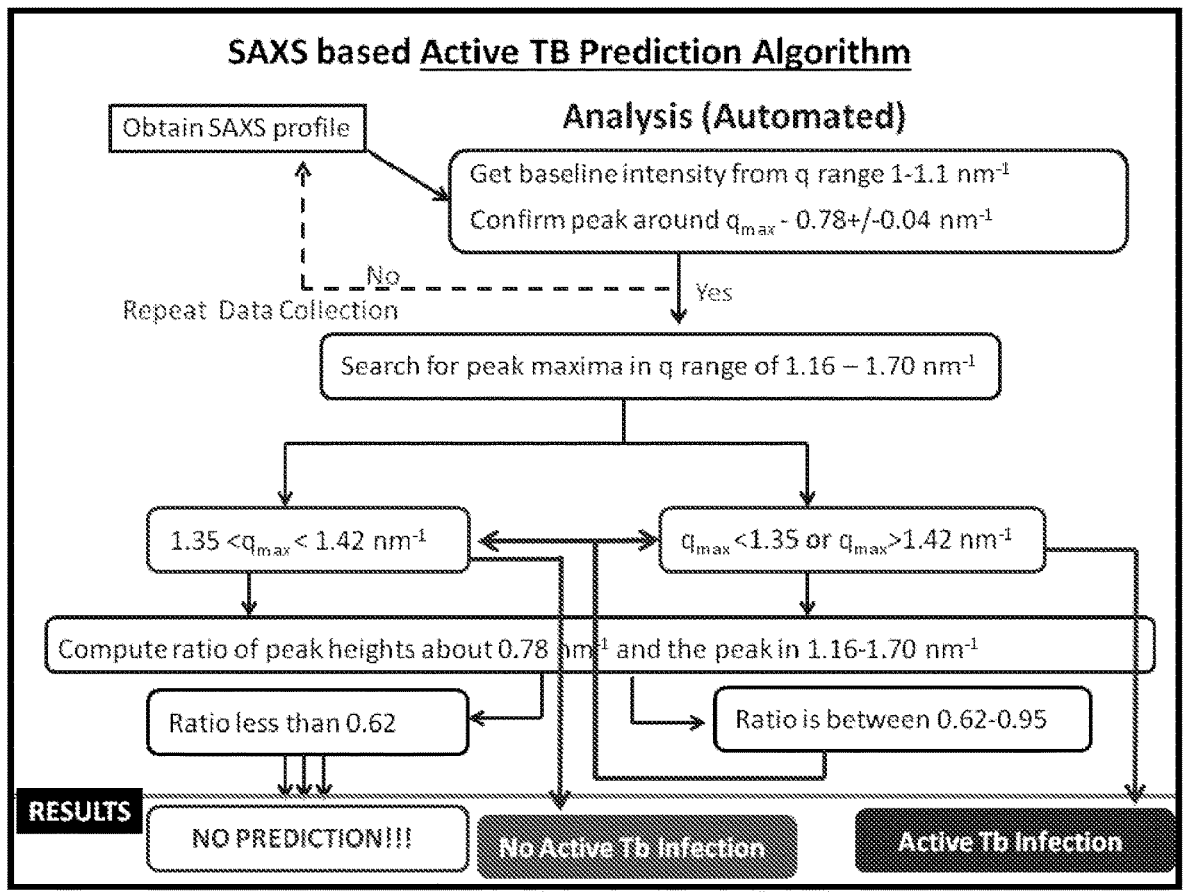

4) Data processing: A program written as per the following the flow chart of information is as shown in FIG. 5.

EXAMPLES

The following examples are given by way of illustration of the present invention and therefore should not be construed to limit the scope of the present invention.

Example 1

Desmeared Representative Hair SAXS Profile from Healthy Donors

Figure 1:
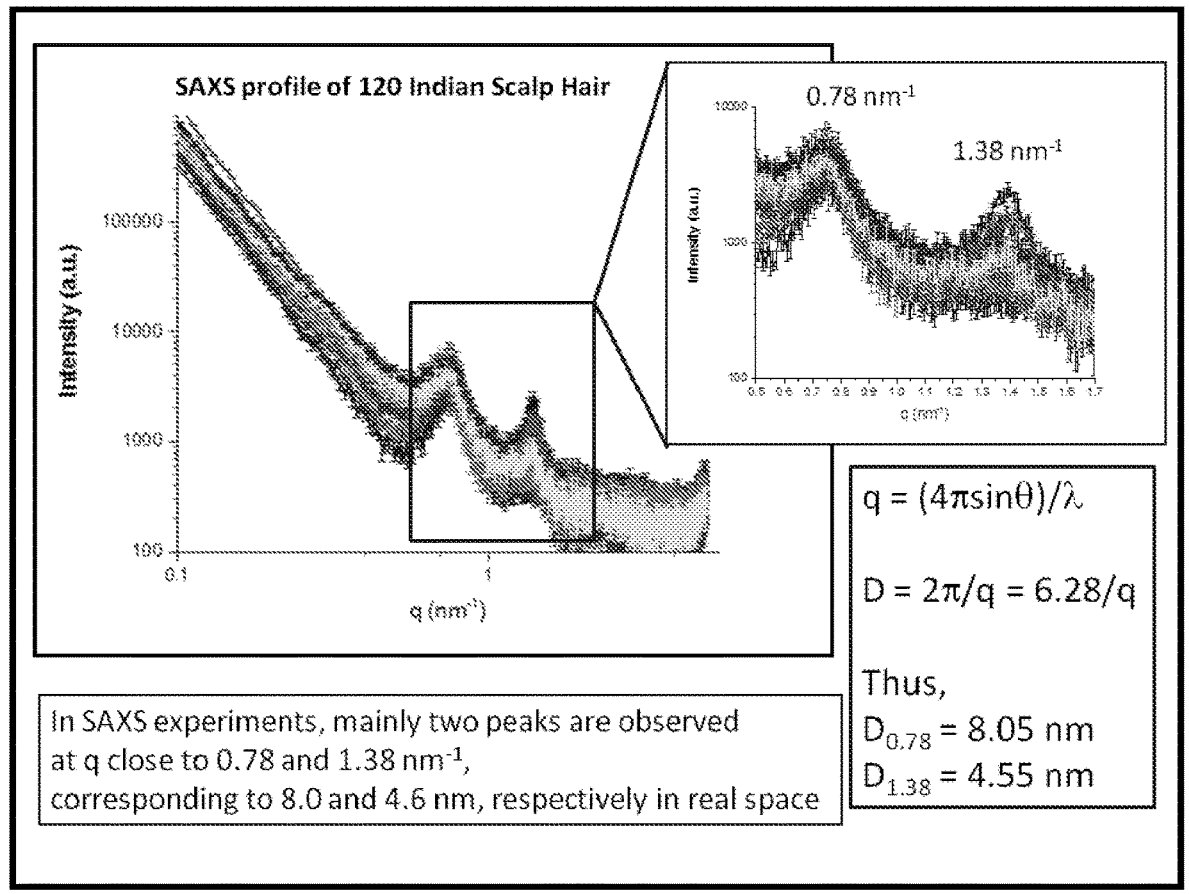

SAXS profiles of scalp hairs of 120 informed donors not suffering any medical issue were obtained. The change in the intensity profile as a function of q were plotted (FIG. 1). Mainly two peaks were observed close to 0.78 and 1.38 $nm^{-1}$. Considering the relationship between momentum transfer vector q and real dimension D, the two peaks correspond to real dimension of 8.05 and 4.55 nm, respectively. Literature analysis indicates that peak corresponding to 0.78 $nm^{-1}$ or 8.05 nm arises from keratin microfilament and other peak with maxima at 1.38 $nm^{-1}$ or 4.55 nm arises from lipid bilayer arrangements. Both these chemical constituents and their macro-organization is basic to the structure of hair.

Example 2

Desmeared SAXS Profiles of Five Different Scalp Hairs from Donors

Figure 2:
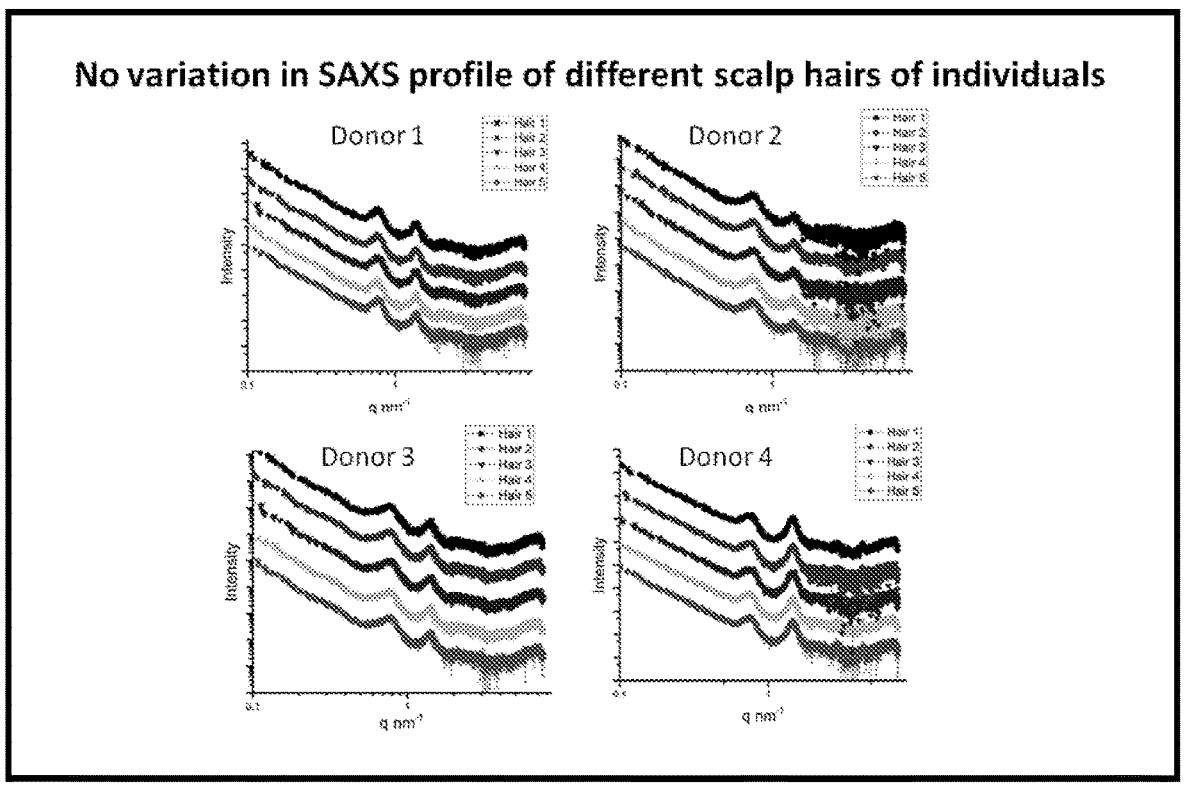

To confirm that all hair from scalp from each donors have similar scattering profile, SAXS profiles from five different hairs from four different donors were collected and compared (FIG. 2). Peak positions, their individual and relative intensities were identical. Thus, any scalp hair would be able to provide representative profile of all other hairs.

Example 3

Desmeared SAXS Profiles of Hair Post-Cosmetic Treatments

Figure 3:
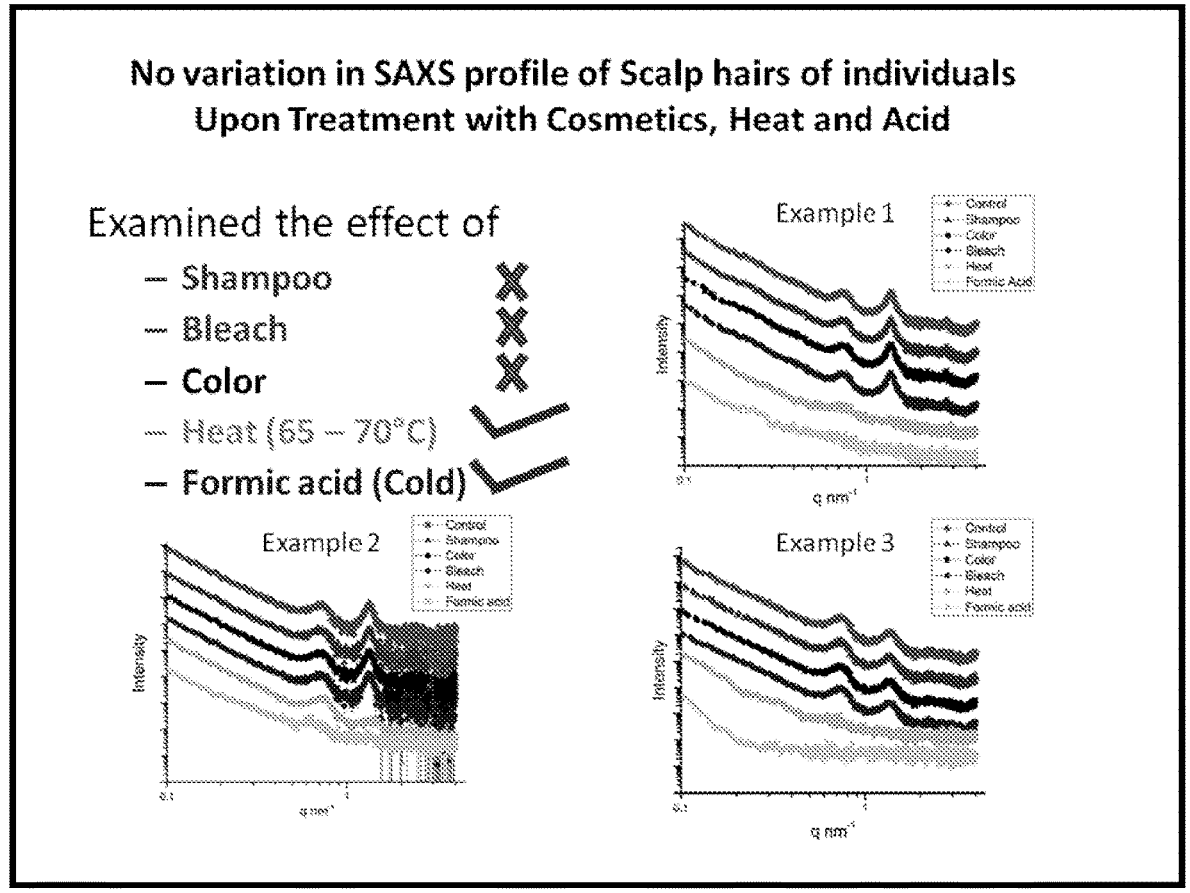

Hair samples were treated with shampoo (commercial brand for 5 minutes, washed thrice with distilled water, air dried at room temperature), bleach (commercial brand for 5 minutes, washed thrice with distilled water, air dried at room temperature), color (blue black commercial color, washed thrice with distilled water, air dried at room temperature), heat (65-70° C. for 5 minutes in oven), and cold formic acid (10° C., 1 N, washed thrice with distilled water, air dried at room temperature). Compared to control, hair SAXS profiles were not affected by shampoo, bleach and color for all three donors tested. Heating and formic acid removed the structure factor peaks seen in hairs. This concluded that usual cosmetic treatments do not affect the predominant hair SAXS profile (FIG. 3).

Example 4

Differential Positioning of the Peaks in Healthy and Mtb +ve Cases

Figure 4:
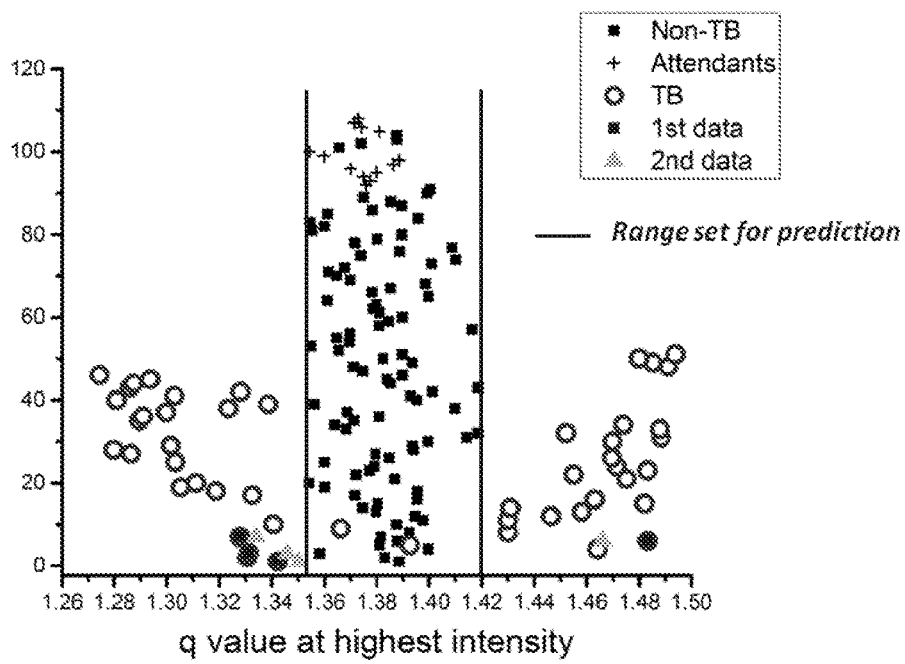

Confirming that the peak close to 0.78 $nm^{-1}$ or 8.05 nm was present, the peak position of the second peak was plotted for about 173 hair samples (120 non-Mtb including 17 close contacts of Mtb +ve, but Mtb –ve in PPD and sputum smear, and 45+8=53 Mtb +ve). The trend indicated that all the Mtb –ve hair and 2 Mtb +ve samples showed the peak arising from lipid content in the range of 1.28-1.48 $nm^{-1}$ or 8.85-7.57 nm, respectively. Remaining Mtb +ve hair samples showed the lipid peak has maxima below 1.28 $nm^{-1}$ or higher than 4.91 nm, or higher than 1.48 $nm^{-1}$ or lower than 4.24 nm. Eight samples were done where hairs were collected twice from 4 patients, once at the time of first identification of Mtb infection and a month later after being on anti-Mtb therapy (blue and green symbols). Data collected till now indicated a shift in the q position of the peak towards 1.38 $nm^{-1}$ or 4.55 nm after therapy. (FIG. 4).

Example 5

Algorithm Used for Data Analysis and Prediction

FIG. 5 shows the data processing flow being followed to interpret if SAXS profile of scalp hair could be a read-out for presence or absence of active *tuberculosis* in host.

ADVANTAGES OF THE INVENTION

1. No prior art connects SAXS of hair to interpret *Mycobacterium tuberculosis* infection.
2. A stretch of hair segment, about 3 cm was exposed to X-ray radiation which provided analysis of a small section of sample hair for Mtb detection over a period of time. Significantly differing from previous prior art and actually serving as an advantage, the present invention acquires SAXS from about 4 cm of hair length, usually closer to the scalp. This provides a wider and average view into the scattering pattern covering 1-2 months of patient's history.
3. In the present invention, sealed tube source which is much cheaper and practical in maintenance has been used in line collimation to compensate for lower incident flux and obtain similar to synchrotron and better than rotating anode based signal to noise ratio in comparable and less exposure times.
4. All previous methods are 2D image analysis based, while in in the present invention circular integration steps are being considered
5. Aligning a fibre parallel to line collimated X-ray was the major challenge and was achieved by overcoming designing integrated mobile platform with three parallel pin diodes which allow alignment and data collection in automated manner from not one but ten hair samples.
6. Further the major advantage is the skill involved in settings to obtain structure factors arising from internal architecture of hair and correlate information with Tb infection.
7. The present invention provides the parameters to avoid skewing of scattering profiles to avoid improper alignment of the hair in terms of the sample to detector distance and incident.

8. Another advantage of the invention is that it can provide assistance to healthcare provider to monitor completion of therapy and/or identify cases of relapse.
9. Most important advantage is that our invention is non-invasive in nature of the diagnosis or screening protocol, the sample cannot be cross-contaminated and the sample under study i.e. hair of the host to be studied can be transported to the site of examination without the need for patient to be actually there.

REFERENCES

1. Pal, R., Hameed, S., Kumar, P., Singh, S., and Fatima, Z. (2017) Comparative lipidomics of drug sensitive and resistant *Mycobacterium tuberculosis* reveals altered lipid imprints. 3 *Biotech* 7, 325
2. Jain, M., Petzold, C. J., Schelle, M. W., Leavell, M. D., Mougous, J. D., Bertozzi, C. R., Leary, J. A., and Cox, J. S. (2007) Lipidomics reveals control of *Mycobacterium tuberculosis* virulence lipids via metabolic coupling. *Proc Natl Acad Sci USA* 104, 5133-5138

We claim:

1. A non-invasive in-vitro method for detecting active *Mycobacterium tuberculosis* (Mtb) using small angle X-ray scattering (SAXS) of a hair sample, wherein presence of keratin peak maxima at 0.78 $nm^{-1}$ or 8.05 nm, and presence of lipid peak above or below the range of 1.28-1.48 $nm^{-1}$ or 4.91-4.24 nm confirms the presence of active Mtb, wherein said method comprises the steps of:

a. mounting the hair sample in a SAXS sample holder;
b. aligning the hair sample with an X-ray beam to be emitted on an integrated mobile platform using a read-out at three PIN diodes, wherein the integrated mobile platform obtains alignment and prior data collection in an automated manner from ten other hair samples;
c. emitting the X-ray beam on the hair sample;
d. acquiring SAXS data from the hair sample;
e. detecting the SAXS data received at a detector of X-rays;
f. analyzing peak profiles arising from keratin and lipid content in the hair sample; and analyzing positions of two peaks in the hair sample, wherein presence of keratin peak maxiama at 0.78 $nm^{-1}$ or 8.05 nm, and presence of lipid peak above or below the range of 1.28-1.48 $nm^{-1}$ or 4.91-4.24 nm confirms the presence of active Mtb.

2. The method according to claim 1, wherein SAXS is performed using a source of monodisperse X-rays with optics selected from a group having line, point, elliptical and rectangle collimation of X-rays on the hair sample.

3. The method according to claim 2, wherein for line source collimation, the source of monodisperse X-rays is a sealed tube source.

4. The method according to claim 1, wherein the SAXS data is detected on the detector of X-rays selected from a group consisting of X-ray sensitive films, CCD, 1D, and 2D detector.

5. The method according to claim 1, wherein the hair sample is in the range of 3 cm to 4 cm in length.

* * * * *